United States Patent
Wadleigh et al.

(10) Patent No.: US 8,093,183 B2
(45) Date of Patent: Jan. 10, 2012

(54) METHODS FOR USING POLYOL ESTERS TO CONTROL PESTS

(75) Inventors: Richard W. Wadleigh, Racine, WI (US); Robert E. Perry, Racine, WI (US); Peter J. Schroeder, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 2037 days.

(21) Appl. No.: 11/071,032

(22) Filed: Mar. 3, 2005

(65) Prior Publication Data

US 2005/0197317 A1    Sep. 8, 2005

Related U.S. Application Data

(60) Provisional application No. 60/551,289, filed on Mar. 8, 2004.

(51) Int. Cl.
*A01N 25/02* (2006.01)
(52) U.S. Cl. .................................................. 504/116.1
(58) Field of Classification Search ................ 504/116.1
See application file for complete search history.

(56) References Cited

U.S. PATENT DOCUMENTS

| | | | |
|---|---|---|---|
| 3,470,293 A | 9/1969 | Geiger | |
| 4,888,325 A | 12/1989 | Schroeder et al. | |
| RE33,235 E | 6/1990 | Corsette | |
| 5,196,451 A | 3/1993 | Greig-Smith et al. | |
| 5,756,716 A | 5/1998 | Farone et al. | |
| 6,136,838 A | 10/2000 | Chern et al. | |
| 6,171,608 B1 | 1/2001 | Schmitt et al. | |
| 6,187,842 B1 | 2/2001 | Kobayashi et al. | |
| 6,287,578 B1 | 9/2001 | Duetsch et al. | |
| 6,337,080 B1 | 1/2002 | Fryan et al. | |
| 6,419,941 B1 * | 7/2002 | Farone et al. | 424/405 |
| 6,703,007 B2 | 3/2004 | Glenn, Jr. | |
| 2002/0119171 A1 | 8/2002 | Gruning et al. | |
| 2002/0192257 A1 | 12/2002 | Farone et al. | |
| 2003/0072716 A1 | 4/2003 | Poovathinthodiyil et al. | |

FOREIGN PATENT DOCUMENTS

| | | | |
|---|---|---|---|
| GB | 2119251 A | * | 11/1983 |
| JP | 5039206 A | * | 2/1993 |
| WO | 96/01832 A1 | | 1/1996 |
| WO | WO9601832 | * | 1/1996 |
| WO | 03/014048 A1 | | 2/2003 |

OTHER PUBLICATIONS

Ants[online]. Enchanted Learning, LLC. 1999-2009 [retrieved on Nov. 27, 2009]. Retrieved from the Internet: <URL: http://www.enchantedlearning.com/subjects/insects/ant/Antcoloringpage.shtml>.*
Sheppard et al., 2003, American Bee Journal, 143: pp. 982-985.*
Sheppard, Walter. Re: Apicultural Notes from WSU. In Apis Moleculoar Systematics Laboratory [online]. Washington State University, Feb. 2003; [retrieved on Jan. 25, 2011]. Retrieved from the Internet: <URL:http://apis.wsu.edu/apinotes.html:>.*
G. Puterka, Sugar Esters: A New Insecticide Based on Sugar, U.S.D.A. Fact Sheet, undated, admitted prior art.
AVA Chemical Ventures, Biochemical Pesticide Products, Company News Release, Sep. 5, 2001.

* cited by examiner

*Primary Examiner* — Fereydoun G Sajjadi
*Assistant Examiner* — Courtney Brown

(57) ABSTRACT

Methods are disclosed for killing or knocking down pests selected from the group consisting of cockroaches, ants, bristletails, wasps, hornets, crickets, earwigs, centipedes, scorpions, sowbugs, pillbugs, and spiders. One sprays the pest directly with a solution that is at least 2.8% ester of a polyol (such as sucrose octanoate or sorbitol octanoate). The formulation is designed for use in kitchens, pantries and other areas of the home in which food items may be present. Spray bottle assemblies are also disclosed for delivering the material to the target pest in a desirable manner.

2 Claims, 1 Drawing Sheet

METHODS FOR USING POLYOL ESTERS TO CONTROL PESTS

CROSS-REFERENCE TO RELATED APPLICATIONS

Figure 1:
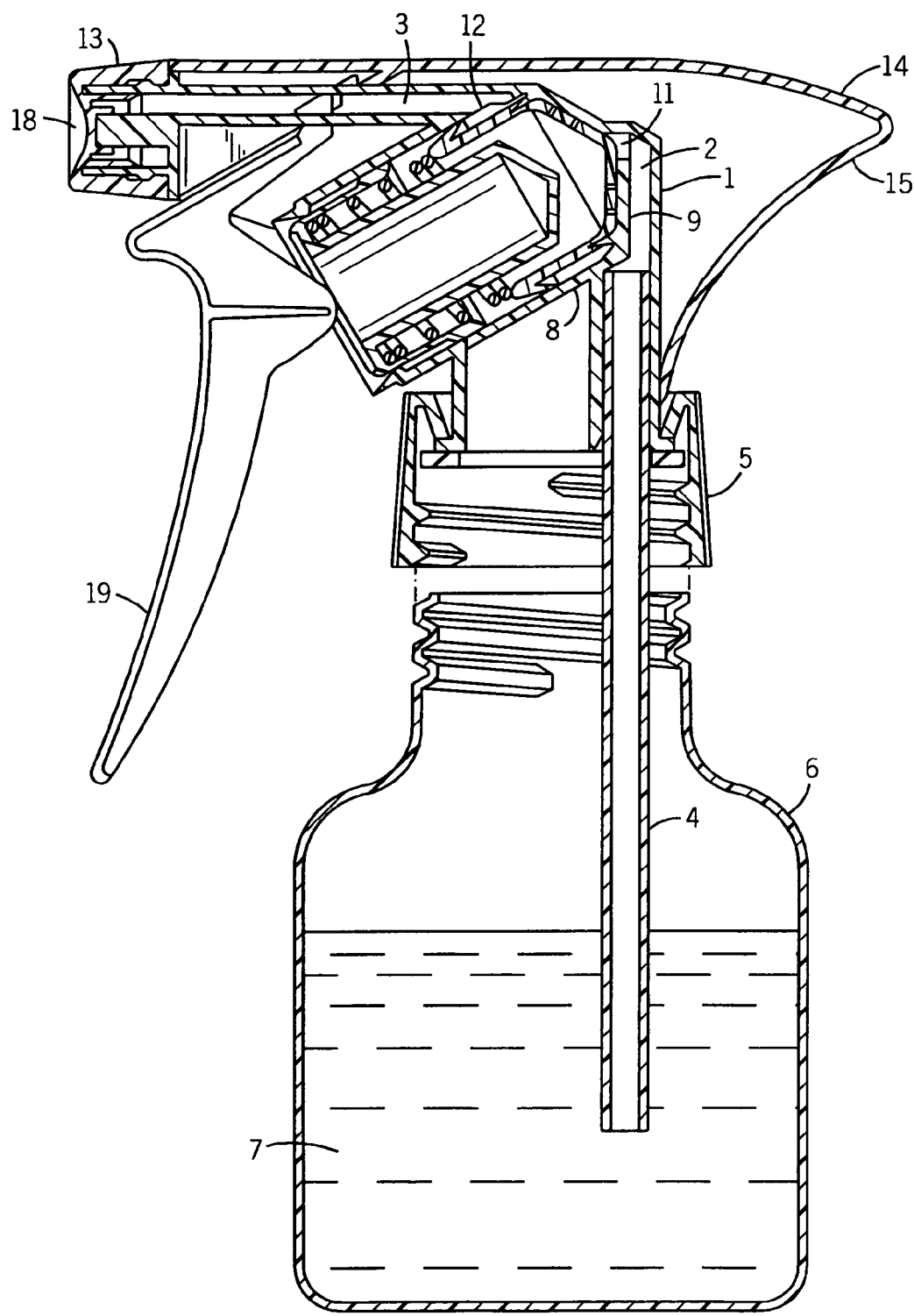

This application claims priority based on U.S. provisional application 60/551,289, which was filed on Mar. 8, 2004.

STATEMENT REGARDING FEDERALLY SPONSORED RESEARCH/DEVELOPMENT

Not applicable

BACKGROUND OF THE INVENTION

The present invention relates to methods for controlling certain insects and other pests by applying solutions of polyol esters, particularly sugar esters, directly to the pests.

A variety of pesticidal formulations are known for controlling insects, and other pests controlled by techniques similar to those used to control insects, in various environments. However, for most of these formulations the formulations contain one or more ingredients that have not previously been recognized as safe for use in connection with foods. Hence, the usage directions for such products, and/or the governmental approvals for using such products, often contain undesirable restrictions. Also the use of such pesticides is sometimes perceived by certain consumers as undesirable (e.g. the organic foods movement).

Some pesticides with improved toxicity and/or degradability characteristics, such as alkyl glycosides, have been developed. See e.g. U.S. Pat. No. 4,888,325. However, they are not optimal for certain uses.

As described in U.S. Pat. No. 6,419,941 (the disclosure of which is hereby incorporated by reference as if fully set forth herein), the art has also discovered a class of polyol esters. Some of these esters are sugar esters that naturally occur in certain plants. Others have been synthesized, such as by using an ester manufacturing process like those described in U.S. Pat. No. 5,756,716. These syntheses typically involved reacting an organic acid with a polyol (preferably a sugar type moiety in ring or linear form) in an esterification reaction, where the polyol contains five to twelve carbons. The polyol ester which results may be a monoester, or may be a mix of monoesters with multiple esterified variants. For purposes of the present invention polyols of sucrose, sorbitol, and xylitol are of greatest interest.

Certain sugar esters have previously been proposed to be used to spray plants/mushrooms so as to control certain soft body/sensitive pests such as psylla, sciarid flies, white flies, scales, hornworms, aphids and spider mites. For example, AVA Chemical Ventures (d/b/a/ Avachem) commercially sells a 40% aqueous solution of sucrose octanoate for spray in diluted form on various plants/mushrooms. In this regard, they suggest diluting it and then spraying a 1.25% to 2.5% solution on mushrooms to control a sciarid fly infestation. Other Avachem literature suggests spraying plants with even lower concentrations of the formulation to control aphids and spider mites.

There have also been prior art suggestions to use such compounds (e.g. sucrose octanoate ester) to control Varroa mites infesting populations of adult honey bees. These compounds were perceived as being safe to the desirable commercial honey bee population, notwithstanding that it could be used to control such mites. Similarly, the USDA has published information on the use of sucrose octanoate which indicates that it is a desirable plant insecticide because it can control certain soft body/sensitive insects while not controlling certain hard body insects that are desirable (such as a lady beetle).

Hence, prior to the present invention, it was generally thought by the art that polyol esters like sucrose octanoate and sorbitol octanoate were not effective pesticides against more resilient types of pests. In fact, the art thought that this selectivity made these compounds particularly desirable for certain purposes.

Thus, a need still exists for pesticidal formulations that can control a variety of resilient insects/pests in an environmentally acceptable way, and improved techniques for using such formulations.

BRIEF SUMMARY OF THE INVENTION

The invention provides a method of killing or knocking down a pest selected from the group consisting of cockroaches, ants, silverfish, firebrats, bristletails, wasps, hornets, crickets, earwigs, centipedes, scorpions, sowbugs, pillbugs and spiders, comprising spraying the pest with a formulation comprising an ester of a polyol. In preferred forms the ester is an ester of an organic acid with a five to twelve carbon polyol, especially where the organic acid has between two and sixteen carbons. For example, the ester could be sucrose octanoate, sorbitol octanoate, sorbitol decanoate, xylitol laurate, and sucrose octaacetate. The most preferred esters may be monoesters, or mixtures of monoesters, diesters and triesters.

Apart from the ester used, we have discovered that it is desirable to directly apply the chemical to the pest, rather than merely applying the chemical to an environment (such as a plant leaf) where the pest might later be. Further, we have discovered that it is important that the animal be contacted with a sufficient amount of the ester by direct spraying (e.g. 0.1 gram or preferably 0.25 gram or more). This can be achieved by spraying the pest with a formulation having a relatively high concentration of the ester (e.g. 2.8% or above) where the spray is a relatively concentrated spray. However, it can also be achieved even with lower concentrations (e.g. 0.5%) where multiple puffs of spray are applied. Thus, a single puff of spray can be sufficient with a 2.8% concentration, whereas multiple puffs might be needed for sufficient treatment at lower concentrations.

The ester is preferably delivered in an aqueous solution (e.g. 80% or more water), and most preferably the solution has nothing in it besides the water and the ester. One way to achieve this would be to acquire from Avachem Chemical Ventures, LLC of Portsmouth, N.H. their 40% aqueous solution of sucrose octanoate (a mixture of mono, di and tri esters), and then dilute it down to a 5% concentration using distilled water, and then place the liquid in a spray bottle such as the Calmar 15508P118 bottle set on a crude spray setting (see also U.S. patent Re. 33,235). One then could spray a pest, such as a cockroach, with the spray from a distance of about 0.1 to 1 meter.

Alternatively, for solubility or other reasons, one may decide to use other solvents besides water for some esters. For example, one could obtain sucrose octanoate from Applied Power Concepts, Inc. of Orange, Calif. They dissolve their mono, di and tri esters in n-butanol. If one starts with a 90% solution in n-butanol water can dilute the solution to the preferred range of concentration.

If an aerosol form is desired, one could add a hydrocarbon propellant (e.g. isobutane/propane mix), plus a small amount of surfactant to create an emulsion or microemulsion, plus corrosion inhibitors, fragrances, or other known aerosol insecticide additives.

It is particularly preferred that the formulation be sprayed from a hand pump spray bottle where the bottle can deliver at least 95% of its spray which reaches a surface which is one meter from the sprayer, within 0.5 meter of a selected target point on that surface. This maximizes the amount of spray contacting the target insect.

In another aspect the invention provides a spray bottle assembly for delivering insecticide. It has an internal cavity containing the above formulation. There is also a trigger-activated pump for pumping the formulation from the cavity to an outlet. Manual activation of the trigger can cause the assembly to spray a surface that is one meter from the outlet such that at least 95% of the spray which reaches that surface will contact the surface within 0.5 meter of a selected point on that surface.

As will be appreciated from the following, the present invention can cause quick knock down of, and ultimately kill, a variety of hard body/more resilient pests common in the home. The control can be achieved with just a water solution of the ester being sprayed on the insect. Hence, the cost of the formulation can be kept reasonable, formulating the formulation is easy, and the formulations will be more widely acceptable with respect to environmental concerns.

The preferred pests to be controlled are crawling insects such as cockroaches and ants. However, the formulations can also be used on nests of flying insects such as wasps.

The foregoing and other advantages of the invention will become apparent from the following description. In the following description reference is made to the accompanying drawing which forms a part thereof, and in which there is shown by way of illustration a preferred embodiment of the invention. This embodiment does not represent the full scope of the invention. Reference should therefore be made to the claims herein for interpreting the scope of the invention.

BRIEF DESCRIPTION OF THE DRAWINGS

FIG. 1 is a sectional/schematic view of a spray bottle capable of delivering the formulations of the present invention in a desirable manner.

DETAILED DESCRIPTION OF THE PREFERRED EMBODIMENTS

A. Spray Bottles

A wide variety of known pump type spray bottles can be used to deliver the formulations. See e.g. U.S. patent Re. 33,235. The most preferred spray bottles are those that have nozzles which direct the spray in a more focused pattern (as distinguished from a widespread fine spray).

FIG. 1 shows an example of one type of spray bottle that would be suitable for use with the present invention. There is a pump assembly 1 having an inlet 2 and an outlet 3. A dip tube 4 extends downward there from.

A cap 5 engages the usual bottle 6 in threaded fashion. Prior to assembling the cap 5 to the bottle 6 the bottle is substantially filled with formulation 7 of the present invention.

As is conventional, the pump assembly 1 has a cylinder 8 having an end wall 9 containing an inlet 11. The outlet port 12 extends to a nozzle section 13. The assembly may be provided with the usual shroud 14 having decorative contoured walls 15.

The outlet portion 18 of the nozzle is configured to provide a directed focused spray. There is also a trigger 19.

In operation, and as is well understood in the art, compression of the trigger 19 pushes the pump assembly components, causing spray to be ejected out the outlet portion 18. The return of the trigger to its rest position permits the chemical 7 to be sucked into the pump chamber.

The novelty of FIG. 1 relates to the chemistry of the chemical 7 and the selection of a nozzle outlet portion 18 which provides a focused spray in connection therewith.

B. Formulations.

In our experiments we created aqueous solutions of sucrose octanoate and sorbitol octanoate by diluting the more concentrated formulations provided by the aforesaid manufacturers. We created varied concentrations ranging from 0.05% through 10%.

C. Testing.

We tested our formulations by spraying them on cockroaches, ants, crickets, silverfish, wasps, bristletails, hornets, centipedes, earwigs, spiders and sowbugs. For example, we found our formulations capable of controlling all these species given direct application of a concentrated spray of the formulation. We found that when spraying about three grams of the formulation containing sucrose octanoate we had essentially no kill at 24 hours for German cockroaches at 0.1% concentration, about 80% kill at 24 hours for German cockroaches at 1% concentration, and 100% kill at 5% concentration.

In other experiments, the average time to achieve knock down of such cockroaches was over a minute at concentrations of only 1%. It was about 19 seconds for a 2% solution, and then at about 16 seconds for concentrations between 3 and 5%. The optimal concentration for application appears to be about 2.8% or above.

Using 5% concentrations, average knock down times of 40 seconds or below were achieved for various other species as well (e.g. ants, crickets, silverfish, wasps, bristletails, and hornets). Hence, the invention is widely applicable to insects and other pests controllable by techniques commonly used to control insects (e.g. centipedes).

Hence, we have discovered that by applying these chemicals directly to even hard body/resistant type pests, in sufficient concentrations of the ester, desirable control can be achieved (both quick knock down and effective kill). We believe that for a typical pest of the specified types a desirable dose to contact the pest is at least 0.1 gram of the ester.

The above description has been that of preferred embodiments of the present invention. It will occur to those that practice the art, however, that still other modifications may be made without departing from the spirit and scope of the invention. For example, the solutions need not be entirely aqueous solutions. Mixes of alcohols, hydrocarbons and water should also be useful. Further, a wide variety of other sugar esters should also have similar results.

INDUSTRIAL APPLICABILITY

The present invention provides methods for controlling a variety of insects and other pests using polyol ester compounds, as well as spray bottles suitable to deliver those compounds in an effective manner.

We claim:

1. A method of killing or knocking down a cockroach comprising:

spraying the cockroach with a formulation comprising a pesticidal ester of a sugar polyol;

wherein the cockroach is contacted by direct spraying with said formulation comprising at least 2.8% of the ester by weight;

whereby the cockroach is killed or knocked down; and
wherein the ester is selected from the group consisting of sucrose octanoate and sorbitol octanoate.

2. A method of killing or knocking down an ant, comprising:
  spraying the ant with a formulation comprising a pesticidal ester of a sugar polyol;
  wherein the ant is contacted by direct spraying with said formulation comprising at least 2.8% of the ester by weight:
  whereby the ant is killed or knocked down; and
  wherein the ester is selected from the group consisting of sucrose octanoate and sorbitol octanoate.

* * * * *